United States Patent [19]

Crozier-Willi et al.

[11] Patent Number: 5,141,958
[45] Date of Patent: Aug. 25, 1992

[54] INHIBITION OF CELL ADHESION FOR REDUCING CANCER CELL METASTASES

[75] Inventors: Gayle Crozier-Willi, Evian, France; Mathilde Fleith, Vevey, Switzerland; Michael Buchanan, Toronto, Canada

[73] Assignee: Nestec S.A., Vevey, Switzerland

[21] Appl. No.: 446,130

[22] Filed: Dec. 5, 1989

[30] Foreign Application Priority Data

Dec. 23, 1988 [CH] Switzerland .................. 4790-88

[51] Int. Cl.$^5$ .................. A61K 31/20; A61K 35/78
[52] U.S. Cl. .................. 514/558; 424/195.1
[58] Field of Search .................. 514/558; 424/195.1

[56] References Cited

U.S. PATENT DOCUMENTS 4,526,793  7/1985  Ingenbleed et al. .................. 426/72
4,888,326 12/1989  Horrobin .................. 514/27

FOREIGN PATENT DOCUMENTS 084172A  4/1982  United Kingdom .

OTHER PUBLICATIONS

Horrobin, David F., "The Reversibility of Cancer: The Relevance of Cyclic AMP, Calcium, Essential Fatty Acids and Prostaglandin El", *Medical Hypotheses*, vol. 6, pp. 469-486, 1980.

Horrobin, D. F., "Cellular Basis of Prolactin Action: Involvement of Cyclic Nucleotides, Polyamines, Prostaglandins, Steroids, Thyroid Hormones, Na/K ATPases and Calcium: Relevance to Breast Cancer and the Menstrual Cycle", *Medical Hypotheses*, vol. 5, pp. 599-620, 1979.

Humphries, Martin J., et al., "A Synthetic Peptide from Fibronectin Inhibits Experimental Metastasis of Murine Melanoma Cells", *Science*, Jul. 1986, pp. 467-470.

Humphries, Martin J., et al., "Investigation of the Biological Effects of Anti-Cell Adhesive Synthetic Peptides that Inhibit Experimental Metastasis of B16-F10 Murine Melanoma Cells", *J. Clin. Invest.*, 81: March, 1988, pp. 782-783, 787-790.

Honn, Kenneth V., et al., "Prostacyclin: A Potent Antimetastatic Agent", *Science*, 212: Mar, 1981, pp. 1270-1272.

*Primary Examiner*—John W. Rollins
*Attorney, Agent, or Firm*—Vogt & O'Donnell

[57] ABSTRACT

Lipids obtained from blackcurrant seed are used for preventing proliferation and dissemination of cancerous metastases in patients.

7 Claims, No Drawings

INHIBITION OF CELL ADHESION FOR REDUCING CANCER CELL METASTASES

This invention relates to the use of a blackcurrant lipid in a dietetic or pharmaceutical composition to prevent the adhesion phenomena responsible for certain thrombo-embolic, inflammatory and cancerous diseases.

BACKGROUND OF THE INVENTION

It is known that polyunsaturated fatty acids of the $\omega 3$ and $\omega 6$ series have very important structural and functional roles. Polyunsaturated fatty acids can be defined by the number of carbon atoms, the number of double bonds and the number indicating the position of the first double bond counting from the methyl group which determines their metabolic family designated $\omega$. Thus, in this nomenclature, dihomogammalinolenic acid (DHLA) is $C20:3\omega 6$, eicosapentaenoic acid (EPA) is $C20:5\omega 3$ and arachidonic acid (AA) is $C20:4\omega 6$. The fatty acids linoleic acid (LA, $C18:2\omega 6$) and alphalinolenic acid (ALA, $C18:3\omega 3$) are the essential precursors of the other acids of the two families which are not synthesized by mammalians. No metabolism allows passage from one family to the other. The conversion of LA or ALA into the respective upper members of the two families is obtained by successive desaturation and elongation with relatively low yields.

The prostaglandins form a family of substances which show numerous biological effects. DHLA, AA and EPA are transformed under the effect of cyclo-oxygenase into prostaglandins of the 1(PG1), 2(PG2) and 3(PG3) series, respectively. The PGS of series 1, 2 and 3 respectively comprise 1, 2 and 3 double bonds in their basic structure of $C_{20}$ fatty acids including a cyclopentene group. Among other properties, the PG1S (emanating from DHLA) are capable of inhibiting the aggregation of blood platelets. By contrast, the eicosanoides of series 2 (emanating from AA), for example PG2, thromboxanes, for example PxA2, promote platelet aggregation. The eicosanoides of series 3 (emanating from EPA) have a similar role to the eicosanoides of series 1.

It is assumed that the effectiveness of EPA and DHLA in the prevention of cardiovascular diseases of the thrombo-embolic type is based on the favourable effects of the PG3S and PG1S compared with the effects of the PG2S.

In addition, the enzyme system lipoxygenase leads to hydroxylated fatty acids and to leucotrienes from the precursors AA and EPA. Recent studies suggest, in particular, that the compounds 13-hydroxyoctadecatrienoic acid (13-HODE), produced by the endothelial cells of the blood vessels, and 12-hydroxyeicosatetraenoic acid (12-HETE), produced by the platelets via the lipoxygenase, play an important part in the mediation of inter-cell adhesion and hence, in the pathogenesis of thromboses, inflammatory diseases and the dissemination of cancerous metastases. In simple terms, adhesion would be influenced by the regulators 12-HETE and 13-HODE positively by AA, the precursor of 12-HETE, and negatively by LA, leading to 13-HODE. In addition, DHLA is not susceptible to the lipoxygenase.

It has been proposed, for example in published French patent application no. 2 553 662, to add to a pharmaceutical composition or to a food product a mixture of a first fatty acid selected from EPA or docosahexaenoic acid (DHA) on the one hand and a second fatty acid selected from DHLA, cis-linoleic acid, gammalinolenic acid (GLA) on the other hand with the object of preventing cardiovascular diseases. In this patent application, the fatty acids in question must have been separately isolated from natural fats by iodination followed by saponification, solvent extraction of the fatty acids, methylation thereof, separation of the methylesters by chromatography and, finally, deiodination. EPA, for example, is obtained in this way from cod liver oil. The production of such a composition is particularly complicated.

In addition, EPA is particularly unstable. Finally, there are some people who cannot bear any recollection of bad tastes coming from fish oil, even in deodorized or encapsulated form.

SUMMARY OF THE INVENTION

It has now been found that, by using a lipid of the blackcurrant, it is possible to provide EPA conjointly with DHLA while depressing the bioavailability of AA without any of the disadvantages associated with ingestion of fish oil, for example an increase in bleeding time which can cause haemorrhages. Very interesting effects are obtained in this way in regard to prevention of the adhesion and aggregation of platelets, thromboses and the dissemination of cancerous metastases.

Accordingly, the present invention relates to the use of a blackcurrant lipid for the preparation of a dietetic or pharmaceutical composition capable of promoting the bioavailability of dihomogammalinolenic acid and eicosapentaenoic acid over the bioavailability of arachidonic acid.

The uses of the lipids of blackcurrant disclosed herein include using the ipis for prevention of diseases of inflammatory origin, for prevention of adhesion of platelets, for prevention of platelet aggregation, for prevention of thrombosis, for prevention of proliferation and dissemination of cancerous metastases and for inhibiting adhesion of immune cells.

In the context of the invention, blackcurrant lipid is understood to be blackcurrant (*Ribes nigrum*) seed oil obtained by extraction from blackcurrant residues and refining, for example as indicated in European patent 92 085 or European patent 137 862, a mixture of fatty acids emanating from the hydrolysis or fractionation of blackcurrant seed oil obtained for example in accordance with European patent 178 442 or European patent application 271 747, a pharmaceutically acceptable salt of the above-mentioned fatty acids, an oil obtained by reesterification of such a mixture of fatty acids with glycerol, a mixture of the above-mentioned lipids.

The blackcurrant lipid may advantageously be protected against oxidation by a fat-soluble antioxidant, for example ascorbyl palmitate, tocopherols, ascorbic acid in the presence of lecithin or a mixture of such antioxidants.

The dietetic compositions may be made up in the form of emulsions, for example sauces, mayonnaises or margarines.

The pharmaceutical compositions may be made up in various forms adapted to the method of administration, for example oral, enteral, rectal or parenteral. For example, they may be made up in the form of capsules, gelatin-coated pills, suppositories or syrups. In the case of enteral or parenteral administration, the compositions are formulated as apyrogenic and sterile, physically and chemically stable solutions or emulsions.

The dose administered depends on the type and seriousness of the disease to be treated. Effective quantities may be from 1 to 25 g blackcurrant lipid and preferably from 2 to 5 g blackcurrant oil per day in a single dose or preferably in 2 to 3 separate doses.

EXAMPLES

The invention is illustrated by the following Examples in which parts and percentages are by weight, unless otherwise stated.

EXAMPLE 1

Incorporation of DHLA and EPA in the tissues

Many pharmacological studies on the ability to modulate the fatty acids of the tissues by diet have used primarily rats as the experimental model. It is known that, in rats or mice, the ingestion of GLA leads to an increase in the incorporation of GLA in triglycerides or of DHLA in the total lipids, but not the phospholipids. By contrast, in human beings, rabbits and guinea pigs, the ingestion of GLA leads to the incorporation of DHLA in the triglycerides and the phospholipids of the blood, in the membrane of the red corpuscles and in all the lipids. For this reason, guinea pigs have been preferred to rats because, being much closer to man in regard to desaturase activity, they reflect better the situation prevailing in human beings. Also, the liver was chosen as the tissue because it represents the major site of fatty acid conversions.

1.1 Experimental Conditions

3 Groups of 7 male guinea pigs each weighing approximately 300 g are formed and are placed in cages of MACROLON. The groups are fed on semi-synthetic diets respectively containing blackcurrant seed oil (HPC), I, walnut oil (WO), II, or lard (L), III, "ad libitum" for 40 days. The WO is selected for comparison with the HPC because it does not contain the acids GLA and stearidonic acid (SA), but more LA, so that the total quantities of ω6 and ω3 and their ratios are comparable in the two oils.

All the animals have free access to water containing 250 mg/l ascorbic acid. After one night without food, the animals are anaesthetized, their livers are removed and rapidly frozen, finely ground and then stored at −80° C. lipids ingested are shown in Tables 1 and 2 below.

TABLE 1

| Composition of the base diet: | |
| --- | --- |
| Ingredient | % |
| Casein | 30 |
| Starch | 20 |
| Sucrose | 10 |
| Glucose | 3.8 |
| Cellulose | 15 |
| Mineral salts | 6 |
| Vitamins | 2.2 |
| Potassium acetate | 2.5 |
| Magnesium oxide | 0.5 |
| Lipid | 10 |

TABLE 2

| Fatty acid composition of the lipids of the diets (in mol-%) | | | |
| --- | --- | --- | --- |
| Fatty acids | HPC | WO | L |
| C14:0 | — | — | 2.7 |
| C16:0 | 7.4 | 8.6 | 32.4 |
| C16:1 | — | — | 3.4 |
| C17:0 | — | — | 0.5 |
| C17:1 | — | — | 0.3 |
| C18:0 | 0.8 | 1.9 | 14.2 |
| C18:1ω9 | 10.4 | 20.8 | 36.7 |
| C18:2ω6 | 48.1 | 57.7 | 8.4 |
| C18:3ω6 | 17.1 | — | — |
| C18:3ω3 | 12.7 | 11.0 | 0.7 |
| C18:4ω3 | 2.6 | — | — |
| C20:1ω9 | 0.6 | — | 0.7 |
| C20:2ω6 | 0.3 | — | — |
| Total ω6's | 65.5 | 57.7 | 8.4 |
| Total ω3's | 15.3 | 11.0 | 0.7 |
| ω6:ω3 ratio | 4.3 | 5.2 | 12.0 |
| Unsaturation index[1] | 207.6 | 169.2 | 59.8 |

Legend
[1]The unsaturation index is the sum of the products a × b where a is the molar percentage of each unsaturated fatty acid and b is the number of double bonds of that particular fatty acid.

1.2 Analysis of the Fatty Acids 1.2.1

The samples are prepared by homogenizing 1 g frozen hepatic tissue in 20 ml of a solvent mixture of chloroform and methanol (ratio 2:1 by volume) and the total lipids (TLS) are extracted after separation of the precipitated solids by filtration, followed by elimination of the solvents.

1.2.2

The TLS are separated into neutral lipids (NLS) and polar lipids (PLS) by passage through a column of silica gel. The non-acidic and acidic fractions are separated from the PLS in ion exchange columns filled with diethylaminoethyl sepharose gel. The fraction of acidic polar lipids is then freed from salts by passage through a column of silica gel.

1.2.3

The NLS are separated into their various components by high-performance thin-layer chromatography (HPTLC) using glass plates coated with silicic acid. The plates are developed with a solvent mixture of petroleum ether, diethyl ether and acetic acid in a ratio by volume of 85:15:0.5, dried in air, sprayed with a 0.005% solution of primuline in acetone (weight/volume) and the bands corresponding to the various lipids are visualized with UV rays. The esters of cholesterol (CES) triglycerides (TGS) and free fatty acids (FFAS) were identified by comparison with standard products and collected in glass tubes closed with Teflon-coated stoppers.

1.2.4

The PLS are separated into their various components by HPTLC on silica gel plates impregnated with a 2% (weight/volume) solution of boric acid in absolute methanol. The plates are developed with a solvent mixture of chloroform, methanol, triethylamine and water in a ratio by volume of 30:25:34:8. The acidic phospholipids phosphatidyl serine (PS), phosphatidyl inositol (PI), cardiolipine (CL), and the non-acidic phospholipids phosphatidyl ethanolamine (PE) and phosphatidyl choline (PC) were visualized in the same way as the neutral lipids, identified by comparison with the standard products and collected as described above.

1.2.5.

The composition of the TGS, CES, FFAS and PLS is determined by gas-phase chromatography of their methylesters. The methylesters are prepared by methylation in known manner and are then extracted with hexane. The peaks of the compounds in the chromatograms obtained are identified by comparison with the chromatograms of standard products.

1.3 Results

The results of analysis of the lipids are shown in Table 3 below:

TABLE 3

| | | TGS | CES | FFAS | CL | PI | PS | PC | PE |
|---|---|---|---|---|---|---|---|---|---|
| | Composition of the fatty acids in the lipid classes of the liver of guinea pigs fed on diet I (mol-%) | | | | | | | | |
| $\omega 6$ | C18:2$\omega$6 | 47.1 | 33.0 | 25.7 | 68.9 | 21.1 | 25.3 | 31.6 | 19.9 |
| | C18:3$\omega$6 (GLA) | 8.1 | 9.1 | 3.6 | 1.5 | 3.2 | 4.0 | 4.5 | 2.7 |
| | C20:3$\omega$6 (DHLA) | 2.3 | 7.0 | 1.4 | 2.1 | 7.5 | 3.6 | 2.7 | 2.3 |
| | C20:4$\omega$6 (AA) | 1.2 | 3.6 | 1.8 | 3.0 | 11.3 | 5.6 | 7.0 | 18.2 |
| $\omega 3$ | C18:3$\omega$3 | 9.2 | 5.2 | 4.8 | 5.5 | 1.5 | 1.4 | 2.2 | 1.9 |
| | C18:4$\omega$3 | 0.6 | 0.3 | 0.4 | — | 0.1 | — | 0.1 | — |
| | C20:5$\omega$3 (EPA) | — | 0.2 | — | — | — | — | 0.1 | 0.2 |
| | C22:5$\omega$3 | 0.1 | 0.1 | 0.2 | — | 0.3 | 1.1 | 0.3 | 1.2 |
| | C22:6$\omega$3 | 0.2 | — | 0.7 | 0.2 | 0.3 | 2.2 | 0.7 | 3.5 |
| | Ratio C20:3$\omega$6 (DHLA) C20:4$\omega$6 (AA) | 1.9 | 1.9 | 0.9 | 0.7 | 0.7 | 0.7 | 0.4 | 0.1 |
| | Unsaturation index | 178 | 172 | 116 | 190 | 137 | 132 | 136 | 172 |
| | Composition of the fatty acids in the lipid classes of the liver of guinea pigs fed on diet II (mol-%) | | | | | | | | |
| $\omega 6$ | C18:2$\omega$6 | 53.8 | 47.2 | 23.7 | 69.4 | 25.1 | 34.0 | 41.3 | 27.0 |
| | C18:3$\omega$6 (GLA) | 0.6 | 0.4 | 0.7 | — | — | 0.1 | — | 0.4 |
| | C20:3$\omega$6 (DHLA) | 0.4 | 1.0 | 0.3 | 0.2 | 1.9 | 0.5 | 0.2 | 0.4 |
| | C20:4$\omega$6 (AA) | 0.8 | 2.3 | 2.0 | 2.5 | 14.8 | 4.7 | 4.6 | 14.4 |
| $\omega 3$ | C18:3$\omega$3 | 9.1 | 6.5 | 4.5 | 4.0 | 1.0 | 1.5 | 2.2 | 1.8 |
| | C18:4$\omega$3 | — | — | 0.1 | — | — | — | — | — |
| | C20:5$\omega$3 (EPA) | — | — | — | — | 0.1 | — | — | 0.1 |
| | C22:5$\omega$3 | 0.3 | — | 0.1 | 0.2 | 0.3 | 0.7 | 0.3 | 1.2 |
| | C22:6$\omega$3 | 0.2 | — | 0.9 | 0.6 | 0.4 | 1.8 | 0.9 | 4.5 |
| | Ratio C20:3$\omega$6 (DHLA) C20:4$\omega$6 (AA) | 0.5 | 0.5 | 0.2 | 0.1 | 0.1 | 0.1 | <0.1 | <0.1 |
| | Unsaturation index | 162 | 150 | 96 | 179 | 133 | 121 | 126 | 167 |
| | Composition of the fatty acids in the lipid classes of the liver of guinea pigs fed on diet III (mol-%) | | | | | | | | |
| $\omega 6$ | C18:2$\omega$6 | 22.4 | 25.5 | 17.7 | 60.4 | 13.7 | 21.1 | 27.5 | 16.0 |
| | C18:3$\omega$6 (GLA) | 0.2 | 0.1 | 0.6 | — | 0.1 | 0.1 | — | — |
| | C20:3$\omega$6 (DHLA) | 0.2 | 0.2 | 0.2 | 0.2 | 2.8 | 0.8 | 0.4 | 0.3 |
| | C20:4$\omega$6 (AA) | 0.7 | 1.7 | 2.7 | 3.5 | 12.7 | 6.7 | 5.2 | 17.5 |
| $\omega 3$ | C18:3$\omega$3 | 1.5 | 0.8 | 2.1 | 0.5 | 0.1 | 0.5 | 0.6 | 0.3 |
| | C18:4$\omega$3 | 0.1 | — | 0.2 | — | — | — | — | — |
| | C20:5$\omega$3 (EPA) | 0.1 | — | 0.2 | — | 0.4 | 0.2 | 0.3 | 0.7 |
| | C22:5$\omega$3 | 0.6 | 0.2 | 0.3 | 0.3 | 0.8 | 1.5 | 0.7 | 2.1 |
| | C22:6$\omega$3 | 0.7 | 0.3 | 1.6 | 1.9 | 1.1 | 4.1 | 2.5 | 10.7 |
| | Ratio C20:3$\omega$6 (DHLA) C20:4$\omega$6 (AA) | 0.3 | 0.1 | 0.2 | 0.1 | 0.3 | 0.1 | 0.1 | <0.1 |
| | Unsaturation index | 104 | 104 | 91 | 170 | 124 | 129 | 119 | 196 |

The above results show that the incorporation of GLA and DHLA is considerably greater in the case of the group fed on diet I containing HPC.

There is no significant difference between the three groups in regard to the incorporation of AA. The result of these two observations is that the DHLA:AA ratio is considerably higher in the case of the ingestion of HPC.

The incorporation of EPA is considerably greater in the case of the ingestion of HPC than in the case of the ingestion of WO in regard to the TGS, CES, PCS and PES. The same observation is true for the ingestion of L in regard to the TGS and CES.

The unsaturation index shows that guinea pigs are capable of largely compensating the difference in unsaturation of the fatty acids of the diets.

In short, the above results show that the ingestion of HPC results in the substantial incorporation of DHLA and in higher DHLA/AA ratios in all the classes of hepatic lipids. In addition, the incorporation of EPA is greater for the regime based on HPC than for the regime based on WO. It follows from this that the potential of the PG1S and PG3S by comparison with the PG2S is clearly demonstrated in regard to HPC.

EXAMPLE 2

Influence of the Ingestion of HPC on the Fatty Acid Composition of the Plasma Lipids in Human Beings A metabolic study is conducted on a 32-year-old man in good health to whom capsules of HPC concentrate enriched with GLA (78%) and SA (16%) are administered for 6 weeks in accordance with the following schedule:

Days 1-20:   3 capsules/day, corresponding to approxi-

| | |
|---|---|
| Days 21-26: | mately 1 g GLA and 250 mg SA/day 10 capsules/day corresponding to approximately 3 g GLA and 0.8 g SA/day |
| Days 27-37: | administration interrupted because of influenza |
| Days 38-42: | 10 capsules/day, corresponding to approx. 3 g GLA and 0.8 g SA/day |

Analysis of the fatty acids of the various classes of blood serum lipids is carried out by gas chromatography of the methylesters in comparison with the control consisting of the mean of a group receiving a placebo. The results are shown in Table 4 below.

TABLE 4

Fatty acid composition of the various classes of serum lipids in mol-% of the HPC concentrate and the control

| | PLS | | FFAS | | TGS | | CES | |
|---|---|---|---|---|---|---|---|---|
| Fatty acids | HPC Concentrate | Control | HPC Concentrate | Control | HPC Concentrate | Control | HPC Concentrate | Control |
| C20:3ω6 (DHLA) | 8.35 | 3.83 | 0.93 | 0.48 | 1.60 | 0.38 | 1.97 | 0.88 |
| C20:4ω6 (AA) | 16.30 | 14.92 | 1.61 | 1.29 | 3.12 | 1.49 | 11.75 | 9.68 |
| C20:3ω6 | 0.51 | 0.26 | 0.58 | 0.02 | 0.51 | 0.25 | 0.17 | 0.09 |
| C20:4ω6 | | | | | | | | |
| C20:5ω3 (EPA) | 0.94 | 0.68 | — | — | 0.58 | 0.27 | 0.91 | 0.65 |
| C22:5ω3 | 1.52 | 1.28 | 0.87 | 0.19 | 0.90 | 0.50 | 0.18 | — |
| C22:6ω3 | 2.52 | 2.76 | 0.57 | 0.15 | 0.36 | 0.19 | 0.45 | 0.43 |

Evaluation of the above results shows that the GLA ingested is incorporated in all the classes of serum lipids and is rapidly metabolized into DHLA and, to a lesser extent, into AA. An increase is observed in the long-chain ω3 fatty acids, particularly EPA, in relation to the control, which seems to suggest that SA is also incorporated.

It may be concluded that the synthesis potential of the PG1S and PG3S is high by comparison with the PG2S when the regime is supplemented with HPC.

EXAMPLE 3

Thrombosis and Adhesion of Blood Platelets 3.1

Study of the incorporation of fatty acids in the arterial walls.

In this Example, guinea pigs are fed on diets containing various lipids over a period of 6 weeks, after which the fatty acid composition of the aortas of the animals is determined. The composition of the principal fatty acids of the lipids of the diets is shown in Table 5 and that of the fatty acids of the aortas in Table 6 below.

TABLE 5

Composition of the principal fatty acids (in mol-%) in the diets containing the lipids

| | HPC | WO | L | FO |
|---|---|---|---|---|
| C14:0 | 0.1 | 0.1 | 1.8 | 3.0 |
| C16:0 | 7.0 | 7.8 | 26.4 | 24.9 |
| C16:1 | 0.1 | 0.1 | 2.1 | 3.3 |
| C18:0 | 1.4 | 2.1 | 15.4 | 12.8 |
| C18:1ω9 | 11.3 | 17.3 | 37.3 | 34.8 |
| C18:2ω6 | 46.0 | 58.5 | 15.4 | 11.9 |
| C18:3ω6 | 16.8 | — | — | 0.1 |
| C18:3ω3 | 14.3 | 13.9 | 1.1 | 2.0 |
| C18:4ω3 | 3.0 | — | 0.2 | 0.4 |
| C20:5ω3 | — | — | 0.1 | 1.7 |
| C22:6ω3 | — | — | 0.2 | 3.2 |
| Total ω6's | 63.0 | 58.5 | 12.6 | 12.7 |
| Total ω3's | 17.3 | 13.8 | 1.8 | 7.3 |
| ω6:ω3 ratio | 3.6 | 4.2 | 8.7 | 1.8 |

Legend:
FO = oil containing 20% fish oil, 70% lard and 10% walnut oil
L = lipid containing 90% lard and 10% grapeseed oil

TABLE 6

Composition of the principal fatty acids (in mol-%) of the aortas of guinea pigs fed on the diets containing the lipids

| | HPC | WO | L | FO |
|---|---|---|---|---|
| C18:1ω9 | 20.46 | 27.60 | 43.19 | 41.76 |
| C18:2ω6 | 30.58 | 32.95 | 6.51 | 5.97 |
| C18:3ω6 | 4.47 | 0.33 | 0.12 | 0.03 |
| C18:3ω3 | 6.07 | 4.10 | 0.71 | 0.64 |
| C20:3ω6 (DHLA) | 1.43 | 0.13 | 0.10 | 0.05 |
| C20:4ω6 | 0.97 | 0.62 | 0.91 | 0.91 |
| C20:5ω3 | — | — | — | 0.01 |

A substantial increase is observed in the level of DHLA where HPC is ingested. This means that the formation potential of the PG1S is increased in the blood vessels.

3.2

Study of the influence of diet on the biological functions of the blood platelets.

The capacity of the blood platelets of guinea pigs marked with [$^3$H]-adenine to adhere to a thrombogenic surface in the form of discs coated with fibronectin is measured after 4 weeks on the diets of Example 3, Table 5. The number of platelets which have adhered to the discs is counted. The results are shown in Table 7 below.

TABLE 7

| | Diet containing the lipids | | | |
|---|---|---|---|---|
| | HPC | WO | L | FO |
| Number of platelets which have adhered to the discs/cm$^2$ × 10$^5$ | 1.9 | 2.3 | 4.0 | 2.3 |

Where HPC is ingested, there is a reduction in adhesion compared with all the other diets, including that containing fish oil.

3.3.

Study of the thrombogenicity of the vessel wall and adhesion of the platelets.

To study the influence of the fatty acids of the regime on the thrombogenicity of the blood vessels, groups of rabbits are fed with the semi-synthetic diets HPC, WO and FO (Table 5, Example 3) and a commercial diet ("chow", C). After 4 weeks of the regime, a lesion is made in the carotid artery of the rabbits fed with HPC, WO and FO. The rabbits are then injected with blood platelets marked with [hu 3H]-adenine from donor rabbits fed on diet C. "In vivo" measurement of the accumulation of the platelets on the wounded artery tests the reactivity of the blood vessel. To discriminate the effect of the regime on the reactivity of the platelets from its effect on the reactivity of the blood vessel, platelets are isolated from the blood of rabbits fed on the 4 diets and their adhesion to discs coated with fibronectin is measured "ex vivo".

The capacity of the blood vessels to synthesize 13-HODE and the capacity of the platelets to synthesize 12-HETE is also determined.

The results are shown in Tables 8 and 9 below.

TABLE 8

| Number of platelets which have adhered to the discs/cm$^2$ × 10$^5$ | Diet containing the lipids | | | Commercial diet |
|---|---|---|---|---|
| | HPC | WO | FO | C |
| In vivo | 36 | 52 | 48 | 69 |
| Ex vivo | 15 | 18 | 9 | 50 |

It can be seen that the thrombogenicity of the blood vessel "in vivo" is lower with the HPC regime and that there is no difference between the WO and FO regimes. The "ex vivo" measurements of the adhesion of the platelets show a reduced platelet reactivity with the HPC, WO and FO regimes compared with the C regime.

TABLE 9

| | Diet containing the lipids | | | Commercial diet |
|---|---|---|---|---|
| | HPC | WO | FO | C |
| Metabolites of the lipoxygenase 13-HODE (ng/cm$^2$ of vessel) | 30.2 | 27.0 | 4.9 | 12.6 |
| 12-HETE (ng/cm$^2$ platelets) | 2.7 | 2.4 | 1.2 | 9.3 |

Legend
ng = nanogram

No difference is observed in the synthesis of 12-HETE by the platelets of the animals fed on the HPC, WO and FO diets. By contrast, the synthesis of 13-HODE by the vessels is greater with the HPC and WO regimes which is consistent with the higher content of linoleic acid in the blood vessels of these two groups and with the anti-adhesive effect of 13-HODE.

EXAMPLE 4

Metastases 4.1

To study the influence of diet on the proliferation and dissemination of metastases, rats are fed on the diets of Example 3, Table 5, except for that containing WO, over a period of 5 weeks.

One group of rats is fed on a standard so-called "chow" diet (C). Tumour cells (Walker 256) are cultured in a medium containing the radioactive nucleotide [$^{125}$I]-uridine marking the tumour cells. The rats are then injected with the cells. The animals are killed 24 hours later and the radioactivity incorporated in the lungs is determined.

The results are shown in Table 10 below.

TABLE 10

| | Diet containing the lipids | | | Commercial diet |
|---|---|---|---|---|
| | HPC | L | FO | C |
| Number of tumour cells × 10$^4$ | 3.6 | 13.1 | 1.0 | 8.5 |

It can be seen that HPC and FO produce the lowest incorporation of tumour cells. It may be assumed that this effect is attributable to an interaction between the tumour cells and the endothelial cells of the inner walls of the blood vessels: there is less inter-cell adhesion.

4.2

A study is conducted in guinea pigs on the basis of the test of Example 3.2, but applied to animals injected beforehand with tumour cells.

The animals are injected with the tumour cells after 4 weeks' ingestion of the diets and are kept on the diets for another three weeks. The capacity of the blood vessels to synthesize 13-HODE is measured by incubating them with LA. The adhesion of the platelets to the discs is determined as in Example 3.2. The number of animals with lesions of the lungs and the number of lesions per lung are also determined. The results are shown in Table 11 below.

TABLE 11

| | Diet containing the lipids | | | |
|---|---|---|---|---|
| | HPC | WO | L | FO |
| Number of platelets which have adhered to the discs/cm$^2$ × 10$^5$ | 3.6 | 6.6 | 7.1 | 4.1 |
| % of lungs with lesions/total | 33 | 40 | 55 | 33 |
| Number of lesions per lung | 8.9 | 9.8 | 21 | 22 |
| Mol-% of 13-HODE in the inner wall of the blood vessels | 9.4 | 8.6 | 5.5 | 2.9 |

It can be seen that, as in the case of the normal animals (Example 3.2), the ingestion of HPC, like that of FO, results in a reduction in the adhesion of the platelets in the animals injected with tumour cells. The number of lungs bearing lesions is lowest for HPC and FO although the number of lesions per lung is distinctly lower for HPC.

However, a histological study has shown that the lesions were of inflammatory origin and non-cancerous. Accordingly, there is less inflammation with HPC.

The analysis results for 13-HODE show an increased presence of this anti-adhesion mediator when the animals are fed with HPC.

EXAMPLE 5

Inflammation

The polynuclear leucocytes (PMNS) play a decisive part in the inflammatory process and, to that end, they have to leave the blood vessels to enter the peripheral tissues. One of the steps leading to this process is their preliminary adhesion to the inner wall of the blood vessels.

This adhesion is observed by studying the attraction between the PNMS isolated from guinea pigs fed on the diets of Example 3, Table 5 and monolayers of endothelial cells on the discs. The results are shown in Table 12 below.

TABLE 12

| | Diet containing the lipids | | | |
|---|---|---|---|---|
| | HPC | WO | L | FO |
| Number of PMNS per disc | 1391 | 1938 | 1310 | 2193 |

It can be seen that the ingestion of HPC results in a weak attraction of the PMNS to the endothelial cells.

We claim:

1. A method for treating cancer metastases comprising administering lipids obtained from seeds of blackcurrant to a human in an amount effective for reducing inter-cell adhesivity of cells for reducing cancer metastases.

2. A method according to claim 1 wherein the lipids are administered in a daily dose of from 1 g to 25 g.

3. A method according to claim 1 wherein the lipids are administered in a form of blackcurrant seed oil in a daily dose of from 2 g to 5 g of the oil.

4. A method according to claim 1 wherein the lipids are administered in a form for oral administration.

5. A method according to claim 4 wherein the lipids are in a form for enteral or parenteral administration.

6. A method according to claim 1 wherein the lipids are administered in a form for rectal administration.

7. A method according to claim 1 wherein the lipids are administered in a form of a dietetic composition.

* * * * *

UNITED STATES PATENT AND TRADEMARK OFFICE
CERTIFICATE OF CORRECTION

PATENT NO. : 5,141,958
DATED : August 25, 1992
INVENTOR(S) : Gayle CROZIER-WILLI, et al.

It is certified that error appears in the above-identified patent and that said Letters Patent is hereby corrected as shown below:

```
Column 2, line 35, delete "ipis" and insert therefor
--lipids--.
```

Signed and Sealed this

Thirty-first Day of August, 1993

*Attest:*

BRUCE LEHMAN

*Attesting Officer*     *Commissioner of Patents and Trademarks*